(12) United States Patent
Shirahama et al.

(10) Patent No.: US 7,736,393 B2
(45) Date of Patent: Jun. 15, 2010

(54) ARTIFICIAL DURA MATER AND PROCESS FOR PRODUCING THE SAME

(75) Inventors: Noriaki Shirahama, Bungoono (JP);
Tomokazu Mukai, Bungoono (JP);
Takao Okada, Kakogawa (JP); Yukari Imamura, Himeji (JP); Yoshimichi Fujiyama, Kakogawa (JP)

(73) Assignee: Kawasumi Laboratories, Inc., Tokyo (JP)

( * ) Notice: Subject to any disclaimer, the term of this patent is extended or adjusted under 35 U.S.C. 154(b) by 453 days.

(21) Appl. No.: 11/578,971

(22) PCT Filed: Apr. 18, 2005

(86) PCT No.: PCT/JP2005/007738

§ 371 (c)(1),
(2), (4) Date: Feb. 13, 2007

(87) PCT Pub. No.: WO2005/102404

PCT Pub. Date: Nov. 3, 2005

(65) Prior Publication Data

US 2007/0233275 A1 Oct. 4, 2007

(30) Foreign Application Priority Data

Apr. 19, 2004 (JP) ............................ 2004-122852

(51) Int. Cl.
*A61F 2/02* (2006.01)
*A61F 2/00* (2006.01)
*A61B 17/00* (2006.01)
*A61L 15/10* (2006.01)
*C08G 63/91* (2006.01)
*C08G 65/332* (2006.01)
*C08G 63/08* (2006.01)
*C08L 67/04* (2006.01)

(52) U.S. Cl. ............. 623/23.72; 623/11.11; 623/23.75; 623/926; 606/151; 606/154; 600/37; 523/105; 523/113; 523/206; 525/411; 525/413; 525/415; 528/354

(58) Field of Classification Search ............. 623/23.72, 623/11.11, 23.75, 926; 523/111, 115, 206, 523/103, 105; 606/151, 154; 525/411, 413, 525/415; 528/354
See application file for complete search history.

(56) References Cited

U.S. PATENT DOCUMENTS

| 5,861,034 A * | 1/1999 | Taira et al. ............... 623/11.11 |
| 6,441,073 B1 * | 8/2002 | Tanaka et al. ............... 524/414 |
| 2004/0082755 A1 * | 4/2004 | Erneta et al. ............... 528/354 |

FOREIGN PATENT DOCUMENTS

| JP | 03 205059 | 9/1991 |
| JP | 2000 191753 | 7/2000 |
| JP | 2003 199817 | 7/2003 |
| WO | 99 17815 | 4/1999 |
| WO | 03 020330 | 3/2003 |

OTHER PUBLICATIONS

English machine translation of Ono et al. JP 2003199817 A.*

* cited by examiner

*Primary Examiner*—Mark Eashoo
*Assistant Examiner*—Michael Pepitone
(74) *Attorney, Agent, or Firm*—Oblon, Spivak, McClelland, Maier & Neustadt, L.L.P.

(57) ABSTRACT

Provided are an artificial dura mater having a laminated constitution of at least two layers of in vivo degradable polymers, at least one layer of them being a substrate layer, the substrate layer being formed of a lactic acid/glycolic acid/ε-caprolactone copolymer, the copolymer having a component molar ratio of 60-85:3-15:10-30 mol % and the copolymer having an average chain length that satisfies the following expressions (1) to (3) and a process for the production thereof, and when this artificial dura mater is used, no liquid leakage is caused since the bloating of suture holes is small, and the period of time for which it retains its strength is suitably a little longer than the period of time required for the regeneration of an autodura mater, $$2 < L(LA) < [LA\%/(LA\%+GA\%+CL\%)] \times X \times 0.058 \quad (1)$$

$$1 < L(GA) < [GA\%/(LA\%+GA\%+CL\%)] \times X \times 0.58 \quad (2)$$

$$1 < L(CL) < [CL\%/(LA\%+GA\%+CL\%)] \times X \times 0.58 \quad (3)$$

wherein L(LA), L(GA) and L(CL) represent average chain lengths of lactic acid units, glycolic acid units and of caprolactone units, LA%, GA% and CL% represent molar ratios of a lactic acid component, a glycolic acid component caprolactone component in the copolymer and X is a polymerization degree of the copolymer.

9 Claims, 1 Drawing Sheet

ARTIFICIAL DURA MATER AND PROCESS FOR PRODUCING THE SAME

TECHNICAL FIELD

This invention relates to an artificial dura mater as a prosthesis for a dura mater defect in the field of cerebral surgery and a process for the production thereof.

BACKGROUND ART

A dura mater is a membrane that is present between a brain and a cranial bone and that has the functions of brain protection, cerebrospinal fluid protection and the like. In the craniotomy in the cerebral surgery, a dura mater is necessarily dissected, and it is required to provide a prosthesis for the defect or contract that is thereby caused on the dura mater. For the above prosthesis, conventionally, a human dried dura mater was used. However, the Ministry of Health and Welfare has prohibited the implantation thereof since 1997 for a reason that it may cause the contagion of Creutzfeldt-Jakob disease (CJD).

Artificial dura maters using a stretched fluorine-containing resin (polytetrafuloroethylene) or a silicone resin as a material have been developed as a substitute for the human dried dura mater. Since, however, these plastic materials constituting dura maters are generally in vivo non-degradable polymer materials, it has been reported that they persistently remain in a body to stimulate surrounding tissues chronically and hence cause the thickening of a granulation tissue and internal hemorrhage in the skin.

Further, it has been attempted to produce an artificial dura mater from collagen or gelatin as a main material. However, there is involved a problem that the strength thereof against suturing is deficient and that they cannot retain the membrane strength which is required till the regeneration of a dura mater.

The applicants in JP-A-2003-199817 have proposed an artificial dura mater formed by stacking two or more in vivo degradable synthetic polymer layers. This laminated material has at least one "leakage preventing layer" for preventing the leakage of cerebrospinal fluid from artificial dura mater needle holes. However, the above artificial dura mater has a structure in which two layers having different performances (an elastic layer and a form-retaining layer) are stacked in addition to the above leakage preventing layer, so that the problem with the above artificial dura mater is that its production steps are complicated and that it requires a higher cost.

Artificial dura maters formed of in vivo degradable synthetic polymers, which have been so far proposed, have too high biocompatibility, and there is concern that it may adhere to a brain surface. In a traumatic bran injury in particular, intense bleeding is involved, and the problem with them is that they have a particularly high risk of adhesion. In the above traumatic brain injury, further, the frequency of carrying out the craniotomy again is high. However, when the brain surface and the artificial dura mater should adhere, there is a big problem that makes maneuver of the craniotomy difficult.

Further, Japanese Patent 3,453,648 describes a copolymer that is formed from lactide and glycollide and that has a reduced content of a metal having detrimental effects on organs, and it is described that the copolymer can be applied to an artificial dura mater. However, the above copolymer from lactide and glycollide cannot give any artificial dura mater capable of efficiently preventing the leakage of cerebrospinal fluid, which this invention seeks to provide.

As described above, the present situation is that those artificial dura maters which have been so far proposed cannot necessarily be said to be sufficient in terms of their performances and production processes.

Under the circumstances, it is an object of this invention to overcome the problems of the above prior techniques. For example, this invention seeks to overcome the problems that it is required to stack two layers (an elastic layer and a form-retaining layer) having different performances in addition to the leakage preventing layers in the artificial dura mater disclosed in the above JP-A-2003-199817, that the production cost thereof is high since the production steps on a large-scale thereof are complicated and that it is difficult to render nil the leakage of cerebrospinal fluid from needle holes in the artificial dura meter composed of a stretched fluorine resin or silicone resin as a material.

Further, as a typical method for producing an artificial dura mater, conventionally, a melt-molding method is employed. A lactic acid/glycolic acid/ε-caprolactone copolymer that is a degradable polymer has a problem that it is deteriorated in properties due to a pyrolysis during its melt-molding caused by a remaining metal catalyst used for the polymerization.

It is therefore difficult, by means of the above artificial dura mater, to inhibit the leakage of cerebrospinal fluid for a period required before the regeneration of an autodura mater.

For overcoming the above problems, the present inventors have made diligent studies and as a result arrived at an artificial dura mater that simplifies the production process which could not be accomplished with any conventional artificial dura mater, or that reduces the required number of sheets to be stacked, and that has all of the performances required for an artificial dura mater; (a) it is to have the property showing no leakage which is the function required for an artificial dura mater, in particular it is required to be free of the leakage from needle holes of a suture, said leakage posing a great problem, (b) it is to have a softness close to that of an organic dura mater, (c) it is to be decomposed and absorbed along with the course of tissues repair, (d) it is to be free from adhesion to a brain surface, (e) it is to withstand a suture tension, (f) it is to be free of any deterioration of physical properties during melt-molding, and the like.

DISCLOSURE OF THE INVENTION

According to this invention, the following inventions are provided with regard to an artificial dura mater.

[1] An artificial dura mater comprising a laminate of at least two layers of in vivo degradable polymers, at least one layer of them being a substrate layer, said substrate layer being formed of a lactic acid/glycolic acid/ε-caprolactone copolymer, said copolymer having a lactic acid/glycolic acid/ε-caprolactone component molar ratio of 60-85:3-15:10-30 mol % and the copolymer having an average chain length that satisfies the following expressions (1) to (3), $$2 < L(LA) < [LA\%/(LA\%+GA\%+CL\%)] \times X \times 0.058 \quad (1)$$

$$1 < L(GA) < [GA\%/(LA\%+GA\%+CL\%)] \times X \times 0.58 \quad (2)$$

$$1 < L(CL) < [CL\%/(LA\%+GA\%+CL\%)] \times X \times 0.58 \quad (3)$$

wherein $L(LA)$ is an average chain length of lactic acid units, $L(GA)$ is an average chain length of glycolic acid units, $L(CL)$ is an average chain length of caprolactone units, $LA\%$ is a molar ratio of a lactic acid component in the copolymer, $GA\%$ is a molar ratio of a glycolic acid component in the copolymer, $CL\%$ is a molar ratio of a caprolactone component in the copolymer and $X$ is a polymerization degree of the copolymer.

[2] An artificial dura mater as recited in [1], wherein said copolymer has a metal content of 60 ppm or less.

[3] An artificial dura mater as recited in [1] or [2], wherein said copolymer has a monomer content, as a total content of lactic acid, glycolic acid and ε-caprolactone, of 40 ppm or less.

[4] An artificial dura mater as recited in any one of [1] to [3], wherein a fluid leakage from a suture portion is 5 ml/minute or less at a brain pressure of 20 mmHg or less when the artificial dura mater is sutured to an organic brain dura material.

[5] An artificial dura mater as recited in any one of [1] to [4], wherein a hydrophilic polymer layer is stacked on one surface or both surfaces of said substrate layer, the hydrophilic polymer layer being a stacked material layer that works to prevent adhesion thereof to a brain surface.

[6] An artificial dura mater as recited in any one of [1] to [5], wherein the hydrophilic polymer constituting said stacked material layer is a water-swelling polymer.

[7] An artificial dura mater formed by stacking two or more layers of in vivo degradable polymers by melt-molding, at least one layer of substrate layers being formed of a lactic acid/glycolic acid/ε-caprolactone copolymer, said copolymer having a lactic acid/glycolic acid/ε-caprolactone component molar ratio of 60-85:3-15:10-30 mol %, the copolymer having a metal content of 60 ppm or less and having a monomer content, as a total content of lactic acid, glycolic acid and ε-caprolactone monomers, of 40 ppm or less.

According to this invention, further, there are provided the following inventions directed to the process for the production of an artificial dura mater.

[8] A process for the production of an artificial dura mater having a substrate layer, which comprises the steps, for producing said substrate layer, of (1) carrying out polymerization to produce a lactic acid/glycolic acid/ε-caprolactone copolymer with a component molar ratio of 60-94:3-20:3-37 mol %, (2) adding a monomer mixture for constituting a lactic acid/glycolic acid/ε-caprolactone copolymer to the copolymer in (1) to obtain a lactic acid/glycolic acid/ε-caprolactone copolymer having a lactic acid/glycolic acid/ε-caprolactone component molar ratio of 60-85:3-15:10-30 mol % as a final product, and (3) forming the above substrate layer from the copolymer obtained by the above steps (1) and (2).

[9] A process for the production of an artificial dura mater, which comprises stacking hydrophilic polymer layer on one surface or both surfaces of the substrate layer produced in [8], the hydrophilic polymer layer being a stacked material layer that works to prevent adhesion thereof to a brain surface.

PREFERRED EMBODIMENTS OF THE INVENTION

Preferred embodiments of the invention will be explained in detail hereinafter.

(Content of Artificial Dura Mater)

The artificial dura mater of this invention is constituted by stacking at least two layers of in vivo degradable polymers, at least one layer thereof being a substrate layer, said substrate layer being formed of a lactic acid/glycolic acid/ε-caprolactone copolymer, said copolymer having a lactic acid:glycolic acid:ε-caprolactone component molar ratio of 60-85:3-15:10-30 mol %, the copolymer having an average chain length that satisfies the following expressions (1) to (3), $$2 < L(LA) < [LA\%/(LA\%+GA\%+CL\%)] \times X \times 0.058 \tag{1}$$

$$1 < L(GA) < [GA\%/(LA\%+GA\%+CL\%)] \times X \times 0.58 \tag{2}$$

$$1 < L(CL) < [CL\%/(LA\%+GA\%+CL\%)] \times X \times 0.58 \tag{3}$$

wherein $L(LA)$ is an average chain length of lactic acid units, $L(GA)$ is an average chain length of glycolic acid units, $L(CL)$ is an average chain length of caprolactone units, $LA\%$ is a molar ratio of a lactic acid component in the copolymer, $GA\%$ is a molar ratio of a glycolic acid component in the copolymer, $CL\%$ is a molar ratio of a caprolactone component in the copolymer and $X$ is a polymerization degree of the copolymer.

(Substrate Layer)

The artificial dura mater of this invention is constituted by stacking at least two layers of in vivo degradable polymers, and the substrate layer constitutes at least one layer of them and is a layer that retains the strength required for an artificial dura mater and that retains or maintains the form of the dura mater. The substrate layer is constituted from an in vivo degradable polymer that is hydrolyzed or enzymatically decomposed in an organ, and this invention particularly uses the above lactic acid/glycolic acid/ε-caprolactone copolymer therefor.

More specifically, the substrate layer is not only a form-retaining layer but also a layer that is to improve the adhesion to a brain dura mater during its suturing, that is to prevent the leakage of cerebrospinal fluid from suture holes during suturing thereof to an organic dura mater and that is to retain the above form for a long period of time when it is decomposed in an organ.

For the above purposes, it is the most suitable to use the above lactic acid/glycolic acid/ε-caprolactone copolymer (to be referred to as "lactic acid/glycolic acid/ε-caprolactone copolymer", or to be simply referred to as "copolymer" or "in vivo degradable polymer", hereinafter). Further, the molar ratio thereof is required to be 60-85:3-15:10-30 mol % as a lactic acid/glycolic acid/ε-caprolactone copolymer molar ratio.

For example, when the molar ratio of the total content of lactic acid and glycolic acid is too high or exceeds 90%, the substrate layer becomes too hard, and as a result, the artificial dura mater as a whole is hard. Undesirably, such an excessively hardened artificial dura mater may possibly impart damage to a brain surface. Further, when the artificial dura mater is sutured to an autodura mater, undesirably, the adhesion thereof to the autodura mater in a sutured portion is poor.

On the other hand, when the molar ratio of the glycolic acid is too high or exceeds 15%, undesirably, the time period for which the artificial dura mater as a whole can retain its form in an organ becomes small, so that it is difficult to retain the form thereof for a period of time required before the regeneration of an inherent dura mater.

Further, when the molar ratio of ε-caprolactone is too high or exceeds 30%, undesirably, the dura mater as a whole is too flexible or soft, so that it cannot withstand a tension during its suturing.

(Average Chain Length)

In this invention, the segment units of the in vivo degradable polymer for constituting the substrate layer are required to satisfy the conditions of "average chain length" defined by the following expressions (1) to (3).

$$2 < L(LA) < [LA\%/(LA\%+GA\%+CL\%)] \times X \times 0.058 \quad (1)$$

$$1 < L(GA) < [GA\%/(LA\%+GA\%+CL\%)] \times X \times 0.58 \quad (2)$$

$$1 < L(CL) < [CL\%/(LA\%+GA\%+CL\%)] \times X \times 0.58 \quad (3)$$

wherein $L(LA)$ is an average chain length of lactic acid units, $L(GA)$ is an average chain length of glycolic acid units, $L(CL)$ is an average chain length of caprolactone units, $LA\%$ is a molar ratio of a lactic acid component in the copolymer, $GA\%$ is a molar ratio of a glycolic acid component in the copolymer, $CL\%$ is a molar ratio of a caprolactone component in the copolymer and $X$ is a polymerization degree of the copolymer.

In the in vivo degradable polymer constituting the artificial dura mater of this invention, the above defined average chain lengths, together with the above specified component molar ratio of the lactic acid/glycolic acid/ε-caprolactone copolymer, are conditions necessary for providing a sheet formed of the above copolymer with the organ-like softness required for an artificial dura mater and also with the rubber-like contracting property, thereby causing suture holes to contract and prevent the leakage of cerebrospinal fluid through the suture holes.

The copolymer for use in this invention is therefore required to satisfy all of the above expression (1) to (3). When a copolymer should fail to satisfy any one of the above expressions (1) to (3), such a copolymer is not preferred for the artificial dura mater of this invention, and cannot be used.

(Metal Content, etc.)

Desirably, the metal content in the in vivo degradable polymer for constituting the substrate layer is 60 ppm or less, preferably 30 ppm or less. The above metal content mainly refers to a content of metals derived from a polymerization catalyst used for the polymerization of the above in vivo degradable polymer, such as tin, zinc, etc., while the metal shall not be limited thereto.

When melt-molding for the production of an artificial dura mater is carried out in the co-presence of a metal whose content in the copolymer exceeds 60 ppm, undesirably, excess pyrolysis takes place and the molecular weight decreases, thereby the artificial dura mater sometimes becomes with only insufficient strength. Further, a large amount of a low molecular weight material as a product by the pyrolysis is formed, and when such an artificial dura mater is implanted in an organ, therefore, the low molecular weight material is decomposed acceleratedly, thereby making it difficult to prevent the leakage of cerebrospinal fluid for a period required before the regeneration of an autodura mater. Moreover, there is also caused a problem that the shelf life or preservation stability of an artificial dura mater is decreased.

The total monomer content of lactic acid, glycolic acid and ε-caprolactone in the in vivo degradable polymer constituting the substrate layer is required to be 40 ppm or less. When the total monomer content exceeds 40 ppm, not only the shelf life or preservation stability of the in vivo degradable polymer is degreased, but likewise the strength thereof is decreased, thereby making the form-retaining in an organ difficult. Further, when the melt-molding for the production of an artificial dura mater is carried out with the presence of over 40 ppm of monomers, excess pyrolysis takes place, which further decreases the strength of the artificial dura mater.

(Membrane Thickness)

The artificial dura mater of this invention is formed as a film-like sheet having the above at least two layers of in vivo degradable polymers. The thickness thereof can be easily controlled depending upon a molding temperature and a molding pressure. When the thickness of the artificial dura mater is too small, the strength thereof is insufficient thereby causing the leakage of cerebrospinal fluid to take place. When thickness thereof is too large, undesirably, the rigidity of the artificial dura mater is too high and hence may cause damage to brain surface. The total thickness of the artificial dura mater is preferably 30 to 1,000 μm. The thickness of the substrate layer is 25 to 990 μm, preferably approximately 50 to 500 μm, and the thickness of each layer of the laminate is 5 to 500 μm, preferably 5 to 200 μm.

(Laminated Structure)

The artificial dura mater of this invention is a laminate (laminated sheet) having at least two layers, produced by stacking a hydrophilic polymer layer on one surface or both surfaces of the above substrate layer formed of the in vivo degradable polymer, the hydrophilic polymer layer being constituted as a stacked material layer that works to prevent adhesion thereof to a brain surface.

The layer constitution of the above artificial dura mater will be further explained with reference to drawings.

Figure 1:
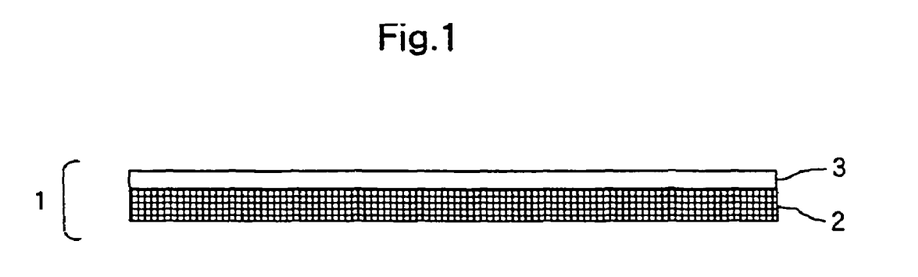
FIG. 1 is a drawing for explaining one example of layer constitution of an artificial dura mater 1 of this invention, in which a stacked material layer 3 is formed on one surface of a substrate layer 2.
Figure 2:
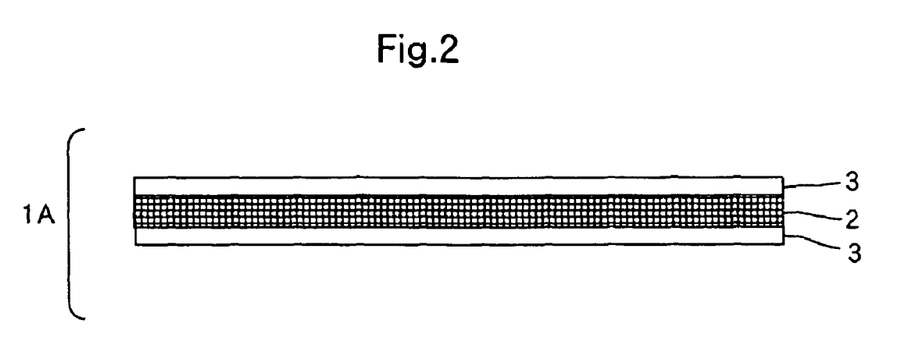
FIG. 2 is a drawing for explaining another embodiment of layer constitution of the artificial dura mater of this invention, in which stacked material layers are formed on both surfaces of a substrate layer 2 one each.
Figure 3:
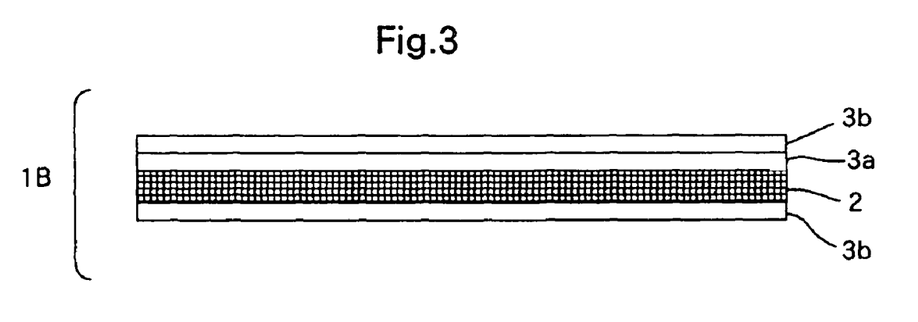
FIG. 3 is a drawing for explaining still another embodiment of layer constitution of the artificial dura mater of this invention, in which a plurality of stacked material layers 3a and 3b are formed on both surfaces of the substrate layer 2.

FIG. 1 is a drawing for explaining one example of the layer constitution of an artificial dura mater 1 of this invention, in which a stacked material layer 3 is formed on one surface of the substrate layer 2. FIG. 2 shows an example of another layer constitution of the artificial dura mater of this invention, in which stacked material layers 3 are formed on both surfaces of the substrate layer 2 one each. FIG. 3 is a drawing for explaining an example of a still another layer constitution of the artificial dura mater of this invention, in which a plurality of stacked material layers 3a and 3b are formed on both surfaces of the substrate layer 2.

The above stacked material layer 3 refers to a layer that is formed of a hydrophilic polymer and that further imparts the artificial dura mater with the function to prevent the leakage of cerebrospinal fluid.

The artificial dura mater of this invention at least has the constitution of double-layer structured or two-layer structured artificial dura mater 1 shown in FIG. 1, a three-layer structured artificial dura mater 1A shown in FIG. 2 or a four-layer structured artificial dura mater 1B shown in FIG. 3, whereby the cerebrospinal fluid leakage preventing function that the substrate layer 2 basically produces is further strengthened by the stacked material layer(s). In addition, the artificial dura mater of this invention can be constituted as a multi-layered structure having over four layers.

The hydrophilic polymer for the stacked material layer 3 on one surface or both surfaces of the substrate layer 2 may be any polymer so long as it is an in vivo degradable hydrophilic polymer. In view of intimate adhesion to an organic tissue and the like, however, a hydrophilic polymer having high affinity to an organ is preferred. The above artificial dura mater therefore intimately adheres to an autodura mater, thereby the leakage of cerebrospinal fluid from an adhesion surface can be suppressed as reliably as possible. Further, the above hydrophilic polymer is most preferably selected from water-swelling polymers such as hyaluronic acid, carboxymethyl cellulose, methyl cellulose, hydroxypropyl cellulose and alginic acid or copolymers thereof. However, any hydrophilic polymer can be used so long as it is hydrophilic, and there can be also used a gel-like glycolic acid/ε-caprolactone copolymer described in the above JP-A-2003-199817. Further, it may be an enzymatically decomposable bioabsorbable polymer composed mainly of collagen, atelocollagen (a product obtained by treating collagen with protease) or gelatin.

In addition, the stacked material layer 3 may have a stacked structure in which a plurality of stacked material layers (3a, 3b, 3c, . . . , 3n) are provided as shown in FIG. 3 instead of a single layer. For example, as a stacked material layer, there may be employed a stacked structure in which one glycolic acid/ε-caprolactone layer 3a is formed and a layer 3b of a hyaluronic acid or carboxylmethyl cellulose is formed.

(Polymerization Method)

The artificial dura mater of this invention is produced by a process comprising the steps of obtaining an in vivo degradable polymer according to the following two-stage polymerization, and the step of forming a substrate layer using the obtained polymer. That is, an artificial dura mater having the above substrate layer is produced by a process comprising the steps of (1) carrying out polymerization to produce a lactic acid/glycolic acid/ε-caprolactone copolymer with a component monomer molar ratio of 60-98:3-20:3-40 mol %, (2) adding a monomer mixture for constituting a lactic acid/glycolic acid/ε-caprolactone copolymer to the copolymer in (1) to obtain a lactic acid/glycolic acid/ε-caprolactone copolymer having a lactic acid/glycolic acid/ε-caprolactone component monomer molar ratio of 60-85:3-15:10-30 mol % as a final product, and (3) forming the above substrate layer from the copolymer obtained by the above steps (1) and (2).

For example, one embodiment of the polymerization method for producing the above lactic acid/glycolic acid/ε-caprolactone copolymer is as follows. In the first stage, a reactor equipped with a thermometer, a nitrogen-introducing tube and an exhaust vent is charged with lactide, glycollide and ε-caprolactone such that the lactic acid/glycolic acid/ε-caprolactone component molar ratio comes to be 60-98:3-20:3-40 mol %. Tin octanoate, tin chloride, dibutyl tin dilaurate, aluminum isopropoxide, titanium tetrapropoxide, diethyl zinc, or the like in an amount of 0.0005 to 0.005 mass % is added thereto, and the ring-opening polymerization thereof is carried out under heat at 100 to 250° C. in the presence of the above catalyst to obtain a copolymer.

In the second stage, a monomer mixture of lactide, glycollide and ε-caprolactone is added to the above polymerization system such that a final product has a lactic acid/glycolic acid/ε-caprolactone component molar ratio of 60-85:3-15:10-30 mol %, and the ring-opening polymerization thereof is carried out at 100 to 250° C.

In the above manner, the copolymer is produced by the two stages, whereby the average chain lengths of monomer units of the above copolymer can be controlled so as to satisfy the expressions (1) to (3) defined in this invention.

The lactic acid/glycolic acid/ε-caprolactone copolymer in the first polymerizing stage is not specially limited, and it may be any lactic acid/glycolic acid/ε-caprolactone copolymer so long as it is produced by a general polymerization method. For example, the above ring-opening polymerization may be replaced with a method in which lactic acid, glycolic acid and ε-caprolactone are directly subjected to polycondensation by dehydration under reduced pressure to obtain the copolymer. In the ring-opening polymerization, further, the monomer materials can be polymerized in a molten state, while these monomers can be also polymerized in a solvent in which they are soluble.

The lactide or lactic acid monomer for use in the ring-opening polymerization or polycondensation by dehydration may be any one of D-configuration, L-configuration and DL-configuration compounds, and a mixture of these may be used.

However, when a monomer or oligomer is present in the thus-obtained lactic acid/glycolic acid/ε-caprolactone copolymer, undesirably, it abnormally promotes the reaction and decomposition of tissues in an organic when the copolymer is used in the organ, and decomposition fragments over absorption and decomposition by macrophage are generated, thereby causing tissue impairments.

When the above copolymer is melt-molded in the co-presence of the above monomer or oligomer, undesirably, excess pyrolysis takes place and the strength of the copolymer is hence decreased, thereby decreasing there is decreased the form-retaining capability that the artificial dura mater is required to have in an organic decreases. It is therefore preferred to render the monomer content in the copolymer substantially nil by repeating a purifying method such as a reprecipitation or the like. Specifically, it is desirable to purify the copolymer until the monomer content is 40 ppm or less, preferably 30 ppm or less, before use.

Further, the lactic acid/glycolic acid/ε-caprolactone copolymer obtained by the above two-stage polymerization has a number average molecular weight in the range of 100,000 to 500,000.

In this invention, particularly importantly, the average chain lengths of the copolymer obtained satisfy the conditions defined by the above expressions (1) to (3). Even when the number average molecular weight is in the above range, the artificial dura mater having excellent properties as an object of this invention cannot be obtained unless the above average chain lengths satisfy the conditions defined in this invention.

(Production of Artificial Dura Mater)

The substrate layer 2 for constituting the artificial dura mater of this invention can be produced by any one of plastic molding methods employed for forming general film or sheets.

According to one example of the method for producing the substrate layer 2, a copolymer for artificial dura mater material containing the lactic acid/glycolic acid/ε-caprolactone copolymer obtained by the above process is dissolved in a solvent such as chloroform, the resultant polymer solution is applied onto a proper base material, the applied polymer solution is air-dried and then the resultant product is released or peeled, and thus obtained the layer in the form of a film or sheet. Or instead, a powder of the above copolymer may be melted and press-molded under heat. Further, in a still another method, the above copolymer is subjected to melt under heat and extrusion-molded through a T-die to form a film or sheet.

Further, the method for laminating the stacked material layer 3 of a hydrophilic polymer on the substrate layer 2 may be any method so long as the stacked material layer can be disposed on the above substrate layer 2 such that the stacked material layer intimately adheres thereto. Examples of the method include melt-welding under heat of the above hydrophilic polymer, coating by dipping of the substrate layer film or sheet in a solution of the above hydrophilic polymer, application or casting of a solution of the above hydrophilic polymer onto the substrate layer, bonding of a film or sheet of the above hydrophilic polymer to the substrate layer with an adhesive, and the like.

Further, a multi-layered film or sheet composed of the substrate layer 2 and the stacked material layer 3 can be formed at once, using a multiple extruder equipped with multiple dies, by melt-extruding the lactic acid/glycolic acid/ ∈-caprolactone copolymer and the hydrophilic polymer through individual die. Similarly, a multi-layered film or the like can be formed by multiple heat lamination or multiple adhesive lamination.

ADVANTAGEOUS EFFECTS OF THE INVENTION

The artificial dura mater of this invention is (1) free from widening of suture holes, thereby securing no liquid leakage without further stacking two layers (an elastic layer and a form-retaining layer) on the "leakage-preventing layer" like the artificial dura mater described in JP-A-2003-199817, and (2) even when it is an artificial dura mater produced by melt-molding, it is expected that the artificial dura mater maintains its strength in an organ for about 3 months or more, which is the most suitable since it is a little longer than the period required for the regeneration of an autodura mater.

EXAMPLES

The present invention will be explained in detail with reference to Examples hereinafter, while the present invention shall not be limited thereto. In addition, % stands for mass % unless otherwise specified.

Example 1

(1) An oligomer obtained by dehydration-based polycondensation of glycolic acid (reagent, supplied by TOKYO CHEMICAL INDUSTRY CO., LTD.) at approximately 180° C. with stirring was distilled under reduced pressure at 250° C. to give glycollide.

In the first stage of polymerization, a reactor equipped with an exhaust vent and a thermometer was charged with 202 g of L-lactide (reagent, supplied by SIGMA-ALDRICH JAPAN K.K.), 10 g of the above glycollide, 38 g of ∈-caprolactone (reagent, supplied by TOKYO CHEMICAL INDUSTRY CO., LTD.) and 0.01 g of tin octanoate (reagent, supplied by SIGMA-ALDRICH JAPAN K.K.) as a catalyst, and the pressure inside the reactor was reduced to $1 \times 10^{-3}$ mmHg with a vacuum pump, followed by polymerization at 150° C. for 24 hours.

(2) In the second stage of polymerization, 64 g of L-lactide, 18 g of the glycollide and 168 g of ∈-caprolactone were added such that a final product was to have a lactic acid/glycolic acid/∈-caprolactone component molar ratio of 67:8:25 mol %, and polymerization was further carried out at 150° C. for 24 hours.

A copolymer obtained by the reaction was dissolved in chloroform and purified by precipitation in methanol, to give a lactic acid/glycolic acid/∈-caprolactone copolymer for use in an artificial dura mater of this invention.

(3) The thus-obtained lactic acid/glycolic acid/∈-caprolactone copolymer was measured for a number average molecular weight by GPC to show 280,000, and its composition (molar ratio) was determined by $^1$H-NMR measurement to show that it had a lactic acid/glycolic acid/∈-caprolactone molar ratio of 67:8:25 mol %.

Further, the average chain lengths of the copolymer were determined on the basis of $^{13}$C-NMR measurement to obtain L(LA)=7.4, L(GA)=5.1 and L(CL)=1.2. Further, the average chain lengths in the expressions (1) to (3) were 2<L(LA) <133, 1<L(GA)<159 and 1<L(CL)<497, so that each average chain length was in the corresponding range defined in the expressions (1) to (3).

As a metal content in the thus-obtained lactic acid/glycolic acid/∈-caprolactone copolymer, the content of tin was 16 ppm as Sn, and as a monomer content therein, the total content of lactic acid, glycolic acid and ∈-caprolactone was 20 ppm.

(4) The thus-obtained lactic acid/glycolic acid/∈-caprolactone copolymer was used for a substrate layer to form an artificial dura mater having a layer constitution shown in FIG. 1. That is, a powder of the above copolymer was press-molded at 160° C. at 30 kg/cm² and cooled with a cooling press machine at 10° C. to give a substrate layer 2 that was a 200 μm thick film-like sheet having rubber elasticity and form-retaining capability. A cast film of hyaluronic acid (reagent, supplied by Wako-Purechemical Ind. Co., Ltd.) was stacked on one surface of the obtained sheet substrate layer 2 to form a stacked material layer 3, whereby a 300 μm thick artificial dura mater 1 composed of two layers was obtained.

Example 2

(1) An oligomer obtained by dehydration-based polycondensation of glycolic acid (reagent, supplied by TOKYO CHEMICAL INDUSTRY CO., LTD.) at approximately 180° C. with stirring was distilled under reduced pressure at 250° C. to give glycollide.

In the first stage of polymerization, a reactor equipped with an exhaust vent and a thermometer was charged with 111 g of L-lactide (reagent, supplied by SIGMA-ALDRICH JAPAN K.K.), 7 g of the above glycollide, 82 g of ∈-caprolactone (reagent, supplied by TOKYO CHEMICAL INDUSTRY CO., LTD.) and 0.01 g of tin octanoate (reagent, supplied by SIGMA-ALDRICH JAPAN K.K.) as a catalyst, and the pressure inside the reactor was reduced to $1 \times 10^{-3}$ mmHg with a vacuum pump, followed by polymerization at 180° C. for 24 hours.

(2) In the second stage of polymerization, 200 g of L-lactide, 18 g of the glycollide and 82 g of ∈-caprolactone were added such that a final product was to have a lactic acid/ glycolic acid/∈-caprolactone component molar ratio of 75:7: 18 mol %, and polymerization was further carried out at 180° C. for 24 hours. A copolymer obtained by the reaction was dissolved in chloroform and purified by precipitation in methanol, to give a lactic acid/glycolic acid/∈-caprolactone copolymer for use in an artificial dura mater of this invention.

(3) The thus-obtained lactic acid/glycolic acid/∈-caprolactone copolymer was measured for a number average molecular weight by GPC to show 350,000, and its composition (molar ratio) was determined by $^1$H-NMR measurement to show that it had a lactic acid/glycolic acid/∈-caprolactone molar ratio of 75:7:18 mol %.

Further, the average chain lengths of the copolymer were determined on the basis of $^{13}$C-NMR measurement to obtain L(LA)=6.3, L(GA)=4.6 and L(CL)=1.9. Further, the average chain lengths in the expressions (1) to (3) were 2<L(LA) <193, 1<L(GA)<180 and 1<L(CL)<464, so that each average chain length was in the corresponding range defined in the expressions (1) to (3).

As a metal content in the thus-obtained lactic acid/glycolic acid/∈-caprolactone copolymer, the content of tin was 20 ppm as Sn, and as a monomer content therein, the total content of lactic acid, glycolic acid and ∈-caprolactone was 18 ppm.

(4) The thus-obtained lactic acid/glycolic acid/ε-caprolactone copolymer was used for a substrate layer to form an artificial dura mater having a layer constitution shown in FIG. 3. That is, a powder of the above copolymer was press-molded at 200° C. at 30 kg/cm² and cooled with a cooling press machine at 10° C. to give a substrate layer 2 that was a 200 μm thick film-like sheet having rubber elasticity and form-retaining capability.

Further, a glycolic acid/ε-caprolactone copolymer (number average molecular weight 68,000) that was a gel-like in vivo degradable polymer was stacked on one surface by heat melt-welding to form a stacked material layer 3a. Further, a cast film of hyaluronic acid (reagent, supplied by Wako-Purechemical Ind. Co., Ltd.) was stacked on both surfaces one each to form stacked material layers 3b and 3b, whereby a 350 μm thick artificial dura mater composed of four layers was obtained.

The glycolic acid/ε-caprolactone copolymer used for forming the above stacked material layer 3a was synthesized by the following method.

A reactor equipped with an exhaust vent and a thermometer was charged with 43 g of glycollide obtained by the above method, 158 g of ε-caprolactone (reagent, supplied by TOKYO CHEMICAL INDUSTRY CO., LTD.) and 0.01 g of tin octanoate (reagent, supplied by SIGMA-ALDRICH JAPAN K.K.) as a catalyst, and the pressure inside the reactor was reduced to $1\times10^{-3}$ mmHg with a vacuum pump, followed by polymerization at 160° C. for 24 hours. A copolymer obtained by the reaction was dissolved in chloroform and purified by precipitation in methanol, to give a glycolic acid/ε-caprolactone copolymer. The thus-obtained glycolic acid/ε-caprolactone copolymer was measured for a number average molecular weight by GPC to show 68,000, and its composition (molar ratio) was determined by ¹H-NMR measurement to show that it had a glycolic acid/ε-caprolactone molar ratio of 40:60 mol %.

Example 3

(1) An oligomer obtained by dehydration-based polycondensation of glycolic acid (reagent, supplied by TOKYO CHEMICAL INDUSTRY CO., LTD.) at approximately 180° C. with stirring was distilled under reduced pressure at 250° C. to give glycollide.

In the first stage of polymerization, a reactor equipped with an exhaust vent and a thermometer was charged with 328 g of L-lactide (reagent, supplied by SIGMA-ALDRICH JAPAN K.K.), 10 g of the glycollide, 112 g of ε-caprolactone (reagent, supplied by TOKYO CHEMICAL INDUSTRY CO., LTD.) and 0.01 g of zinc diethyl (reagent, supplied by KANTO CHEMICAL CO. INC.) as a catalyst, and the pressure inside the reactor was reduced to $1\times10^{-3}$ mmHg with a vacuum pump, followed by polymerization at 145° C. for 24 hours.

(2) In the second stage of polymerization, 10 g of L-lactide, 8 g of the glycollide and 32 g of ε-caprolactone were added such that a final product was to have a lactic acid/glycolic acid/ε-caprolactone component molar ratio of 80:5:15 mol %, and polymerization was further carried out at 180° C. for 24 hours.

A copolymer obtained by the reaction was dissolved in chloroform and purified by precipitation in methanol, to give a lactic acid/glycolic acid/ε-caprolactone copolymer for use in an artificial dura mater of this invention.

(3) The thus-obtained lactic acid/glycolic acid/ε-caprolactone copolymer was measured for a number average molecular weight by GPC to show 180,000, and its composition (molar ratio) was determined by ¹H-NMR measurement to show that it had a lactic acid/glycolic acid/ε-caprolactone molar ratio of 80:5:15 mol %.

Further, the average chain lengths of the copolymer were determined on the basis of ¹³C-NMR measurement to obtain L(LA)=5.9, L(GA)=4.8 and L(CL)=1.6. Further, the average chain lengths in the expressions (1) to (3) were 2<L(LA)<107, 1<L(GA)<67 and 1<L(CL)<201, so that each average chain length was in the corresponding range defined in the expressions (1) to (3).

As a metal content in the thus-obtained lactic acid/glycolic acid/ε-caprolactone copolymer, the content of zinc was 30 ppm as Zn, and as a monomer content therein, the total content of lactic acid, glycolic acid and ε-caprolactone was 26 ppm.

(4) The thus-obtained lactic acid/glycolic acid/ε-caprolactone copolymer was used for a substrate layer to form an artificial dura mater 1A having a layer constitution shown in FIG. 2. That is, a powder of the above copolymer was press-molded at 180° C. at 30 kg/cm² and cooled with a cooling press machine at 10° C. to give a substrate layer 2 that was a 200 μm thick film-like sheet having rubber elasticity and form-retaining capability. Further, cast films of alginic acid (reagent, supplied by Wako-Purechemical Ind. Co., Ltd.) that was a water-swelling polymer were arranged on both surfaces of the thus-obtained film-like sheet one each as a stacked material layer 3, to give a 400 μm thick artificial dura mater (1A) composed of three layers.

Comparative Example 1

(1) A reactor equipped with an exhaust vent and a thermometer was charged with 263 g of L-lactide (reagent, supplied by SIGMA-ALDRICH JAPAN K.K.), 42 g of glycollide (prepared under the same conditions as those in Example 1), 194 g of ε-caprolactone (reagent, supplied by TOKYO CHEMICAL INDUSTRY CO., LTD.) and 0.01 g of tin octanoate (reagent, supplied by SIGMA-ALDRICH JAPAN K.K.) as a catalyst, and the pressure inside the reactor was reduced to $1\times10^{-3}$ mmHg with a vacuum pump, followed by polymerization at 190° C. for 24 hours. After the reaction, a copolymer was dissolved in chloroform and purified by precipitation in methanol, to give a lactic acid/glycolic acid/ε-caprolactone copolymer.

(2) The thus-obtained lactic acid/glycolic acid/ε-caprolactone copolymer was measured for a number average molecular weight by GPC to show 220,000, and its composition (molar ratio) was determined by ¹H-NMR measurement to show that it had a lactic acid/glycolic acid/ε-caprolactone molar ratio of 65:15:20 mol %.

Further, the average chain lengths of the copolymer were determined on the basis of ¹³C-NMR measurement to obtain L(LA)=1.8, L(GA)=1.2 and L(CL)=0.8. Further, the average chain lengths in the expressions (1) to (3) were 2<L(LA)<106, 1<L(GA)<244 and 1<L(CL)<326, and L(LA) and L(CL) were below the lower limits defined by the expressions.

(3) An artificial dura mater was formed according the layer constitution shown in FIG. 1. That is, a powder of the thus-obtained copolymer was press-molded at 200° C. at 30 kg/cm² and cooled with a cooling press machine at 10° C. to give a substrate layer 2 that was a 200 μm thick film-like sheet having rubber elasticity and form-retaining capability. Further, hyaluronic acid that was a hydrophilic water-swelling polymer was arranged on one surface of the substrate layer 2 to form a stacked material layer 3 in the same manner as in Example 1, whereby a 300 μm thick artificial dura mater 1 composed of two layers was obtained.

Comparative Example 2

(1) A reactor equipped with an exhaust vent and a thermometer was charged with 322 g of L-lactide and 0.01 g of tin octanoate as a catalyst, and the pressure inside the reactor was reduced to $1 \times 10^{-3}$ mmHg with a vacuum pump, followed by polymerization at 160° C. for 24 hours. Then, 156 g of ε-caprolactone was added to the reactor, followed by polymerization at 190° C. for 10 hours. Further, 22 g of glycollide was added, and the mixture was heated to 210° C. and polymerized for 24 hours.

After the reaction, a formed product was dissolved in chloroform and purified by precipitation in methanol, to give a lactic acid/glycolic acid/ε-caprolactone copolymer.

(2) The thus-obtained lactic acid/glycolic acid/ε-caprolactone copolymer was measured for a number average molecular weight by GPC to show 200,000, and its composition (molar ratio) was determined by $^1$H-NMR measurement to show that it had a lactic acid/glycolic acid/ε-caprolactone molar ratio of 75:7:18 mol %.

Further, the average chain lengths of the copolymer were determined on the basis of $^{13}$C-NMR measurement to obtain L(LA)=1,830, L(GA)=120 and L(CL)=480. Further, the average chain lengths in the expressions (1) to (3) were 2<L(LA)<110, 1<L(GA)<103 and 1<L(CL)<266, and the average change lengths were all over upper limits defined by the expressions (1) to (3).

(3) The thus-obtained copolymer was used to prepare an artificial dura mater 1 having a layer constitution shown in FIG. 1. That is, a powder of the above copolymer was press-molded at 200° C. at 30 kg/cm$^2$ and cooled with a cooling press machine at 10° C. to give a substrate layer 2 that was a 200 μm thick film-like sheet having rubber elasticity and form-retaining capability. Further, a glycol acid/ε-caprolactone copolymer (number average molecular weight 68,000) that was a gel-like in vivo degradable polymer was stacked in the same manner as in Example 2 to form a stacked material layer 3, whereby a 350 μm thick artificial dura mater 1 composed of two layers was obtained.

The glycol acid/ε-caprolactone copolymer used for the stacked material 3 was synthesized by the same method as that in Example 2.

Comparative Example 3

In the first stage of polymerization, a reactor equipped with an exhaust vent and a thermometer was charged with 130 g of L-lactide, 2 g of glycollide, 50 g of ε-caprolactone and 0.01 g of tin octanoate as a catalyst, and the pressure inside the reactor was reduced to $1 \times 10^{-3}$ mmHg with a vacuum pump, followed by polymerization at 150° C. for 24 hours.

(2) In the second stage of polymerization, 4 g of L-lactide, 10 g of glycollide and 304 g of ε-caprolactone were added such that a final product was to have a lactic acid/glycolic acid/ε-caprolactone component molar ratio of 40:5:55 mol %, and polymerization was further carried out 150° C. for 24 hours. A copolymer obtained by the reaction was dissolved in chloroform and purified by precipitation in methanol, to give a lactic acid/glycolic acid/ε-caprolactone copolymer.

(3) The thus-obtained lactic acid/glycolic acid/ε-caprolactone copolymer was measured for a number average molecular weight by GPC to show 290,000, and its composition (molar ratio) was determined by $^1$H-NMR measurement to show that it had a lactic acid/glycolic acid/ε-caprolactone molar ratio of 40:5:55 mol %.

Further, the average chain lengths of the copolymer were determined on the basis of $^{13}$C-NMR measurement to obtain L(LA)=5.6, L(GA)=1.2 and L(CL)=3.8. Further, the average chain lengths in the expressions (1) to (3) were 2<L(LA)<71, 1<L(GA)<89 and 1<L(CL)<980, so that each average chain length was in the corresponding range defined in the expressions (1) to (3).

(4) The thus-obtained copolymer was used for a substrate layer to form an artificial dura mater according to the layer constitution shown in FIG. 1. A powder of the above copolymer was press-molded at 160° C. at 30 kg/cm$^2$ and cooled with a cooling press machine at 10° C. to give a substrate layer 2 that was a 200 μm thick film-like sheet having rubber elasticity and form-retaining capability. A cast film of hyaluronic acid that was a hydrophilic swelling polymer was stacked by the same method as that in Example 1 to form a stacked material layer 3, whereby a 300 μm thick artificial dura mater 1 composed of two layers was obtained.

Example 4

An oligomer obtained by dehydration-based polycondensation of glycolic acid (reagent, supplied by TOKYO CHEMICAL INDUSTRY CO., LTD.) at approximately 180° C. with stirring was distilled under reduced pressure at 250° C. to give glycollide.

In the first stage of polymerization, a reactor equipped with an exhaust vent and a thermometer was charged with 3 g of L-lactide (reagent, supplied by SIGMA-ALDRICH JAPAN K.K.), 2 g of glycolic acid (reagent, supplied by TOKYO CHEMICAL INDUSTRY CO., LTD.), 55 g of ε-caprolactone (reagent, supplied by TOKYO CHEMICAL INDUSTRY CO., LTD.) and 0.01 g of tin octanoate (reagent, supplied by SIGMA-ALDRICH JAPAN K.K.) as a catalyst, and these monomers were polymerized under reduced pressure at 180° C. for 24 hours.

(2) In the second stage of polymerization, 278 g of L-lactide (reagent, supplied by SIGMA-ALDRICH JAPAN K.K.), 18 g of the above glycollide and 120 g of ε-caprolactone (reagent, supplied by TOKYO CHEMICAL INDUSTRY CO., LTD.) were added such that a final product was to have a lactic acid/glycolic acid/ε-caprolactone component molar ratio of 72:8:20 mol %, and polymerization was further carried out at 150° C. for 24 hours. A copolymer obtained by the reaction was dissolved in chloroform and purified by precipitation in methanol, to give a lactic acid/glycolic acid/ε-caprolactone copolymer for use in an artificial dura mater of this invention.

(3) The thus-obtained lactic acid/glycolic acid/ε-caprolactone copolymer was measured for a number average molecular weight by GPC to show 120,000, and its composition (molar ratio) was determined by $^1$H-NMR measurement to show that it had a lactic acid/glycolic acid/ε-caprolactone molar ratio of 72:8:20 mol %.

Further, the average chain lengths of the copolymer were determined on the basis of $^{13}$C-NMR measurement to obtain L(LA)=4.8, L(GA)=1.2 and L(CL)=2.8. Further, the average chain lengths in the expressions (1) to (3) were 2<L(LA)<64.1, 1<L(GA)<70 and 1<L(CL)<176, so that each average chain length was in the corresponding range defined in the expressions (1) to (3).

As a metal content in the thus-obtained lactic acid/glycolic acid/ε-caprolactone copolymer, the content of tin was 20 ppm as Sn, and as a monomer content therein, the total content of lactic acid, glycolic acid and ε-caprolactone was 16 ppm.

(Performance Evaluation Test)

The artificial dura maters described in the above Examples 1 to 3 and Comparative Examples 1 to 3 were evaluated for the following performances.

Physical Property Evaluation Test

The number n of test samples in each test was 5, and results in each test were averaged.

(1) 10% Tensile Resistance

Each artificial dura mater was cut to 6.35 mm×64 mm, and a tensile test (with a tensile tester supplied by Shimadzu Corporation) was carried out under constant temperature condition of 37° C. at an inter-chuck distance of 20 mm and at a tensile rate of 10 mm/minute with regard to each test piece. When each test piece was stretched by 10%, a tensile resistance of each was recorded.

(2) Bending Resistance

Each artificial dura mater was cut to 6.35 mm×64 mm, and a bending resistance test was carried out in the same manner as in JIS-L1096 with regard to each test piece. The length of each test piece in the test was adjusted to 40 mm.

(3) Permanent Set

Each artificial dura mater was cut to 6.35 mm×64 mm, and each test piece was stretched by 100% under constant temperature condition of 37° C. at an inter-chuck distance of 20 mm at a tensile rate of 10 mm/minute and taken out of the chucks and allowed to stand under a condition of a constant temperature of 37° C., and then a degree of elongation of a stretched portion was measured.

Degradability Evaluation Rest

Degradability test pieces prepared by cutting each artificial dura mater to 6.35 mm×64 mm were immersed in a saline solution and the saline solution with the test pieces therein was kept at 37° C. Test pieces were taken out after 4 weeks, after 8 weeks and after 12 weeks and each subjected to a tensile strength test. The tensile test of each test piece was carried out under conditions of an inter-chuck distance of 10 mm and a tensile rate of 50 mm/minute.

Water Leakage Test

Each artificial dura mater was evaluated for a function of preventing the leakage of cerebrospinal fluid. An artificial dura mater having a length of 50 mm and a width of 25 mm and an organic brain dura mater taken from a pig were continuously sutured to each other with a suture (Vicryl suture, supplied by Ethicon Inc.) with an overlapping width of 5 mm at suturing intervals of 2 mm, and in this manner square test pieces having sides of 50 mm each were prepared. Such a test piece was set in a 47 mm in-line filter holder (supplied by MILLIPORE Corporation), a saline solution bag having a temperature of 37° C. was set at a top entrance port of the in-line filter holder, pressure was applied up to 20 mmHg and 60 mmHg, and a saline solution discharged from a bottom exit port was recovered and measured to determine an amount of water that leaked from sutured portions per minute. The number n of test pieces of each artificial dura mater was 5, and results in the test of each were averaged.

Measurement of Average Chain Length

For average chain lengths of each of in vivo degradable polymers used for substrate layers, polymers were subjected to $^{13}$C-NMR measurement, and the average chain lengths were determined on the basis of the following expressions using the measurement results. Table 1 shows the results.

Average Chain Length of Lactic Acid Units $$L(LA)=(LLL+LLC+CLL+LLG+GLL)/\{(LLC+CLL)/2+(LLG+GLL)/2\}$$

Average Chain Length of Glycolic Acid Units $$L(GA)=(GGG+GGL+LGG)/(GGL+LGG)/2$$

Average Chain Length of Caprolactone Units $$L(CL)=(CCC+CCL+LCC+LCL)/(LCC+LCL)/2$$

In the above expressions, LLL, LLC, CLL, LLG and GLL are integration values of carbonyl carbon of lactic acid units, GGG, GGL and LGG are integration values of carbonyl carbon of glycolic acid units and CCC, CCL, LCC and LCL are integration values of carbonyl carbon of caprolactone units. Table 1 summarizes compositions in Examples and Comparative Examples.

TABLE 1

(Table of compositions)

| Examples | Copolymerization ratio (LA/GA/CL) | Molecular weight (Mn) | Average chain length (LA/GA/CL) |
|---|---|---|---|
| Ex. 1 | 67/8/25 | 280,000 | 7.4/5.1/1.2 |
| Ex. 2 | 75/7/18 | 350,000 | 6.3/4.6/1.9 |
| Ex. 3 | 80/5/15 | 180,000 | 5.9/4.8/1.6 |
| CEx. 1 | 65/15/20 | 220,000 | 1.8/1.2/0.8 |
| CEx. 2 | 75/7/18 | 200,000 | 1830/120/480 |
| CEx. 3 | 40/5/55 | 290,000 | 5.6/1.2/3.8 |

Ex. = Example, CEx. = Comparative Example (Evaluation Test Results)

Tables 2 to 4 summarize the evaluation test results.

TABLE 2

(Evaluation of Physical Properties)

| Ex. and CEx. | 10% Tensile resistance (MPa) | Bending resistance (mN · mm) | Permanent set (%) |
|---|---|---|---|
| Ex. 1 | 0.7 | 63 | 0 |
| Ex. 2 | 1.8 | 125 | 2 |
| Ex. 3 | 4.0 | 332 | 5 |
| CEx. 1 | 0.5 | 20 | 30 |
| CEx. 2 | 4.8 | 1320 | 50 |
| CEx. 3 | 0.2 | 2 | 22 |

Ex. = Example, CEx. = Comparative Example

The results in Table 2 show that the permanent set values in Examples 1 to 3 are smaller than those in Comparative Examples 1 to 3. And, it can be easily deduced that the bloating of suture holes generated during suturing can be suppressed to the minimum thereby the leakage of cerebrospinal fluid can be prevented.

TABLE 3

(Water leakage test)

| Ex. and CEx. | Amount of water that leaked at 20 mmHg (ml/min) | Amount of water that leaked at 60 mmHg (ml/min) |
|---|---|---|
| Ex. 1 | 0 | 1 |
| Ex. 2 | 0 | 0 |
| Ex. 3 | 0 | 2 |
| CEx. 1 | 6 | 18 |
| CEx. 2 | 11 | 48 |
| CEx. 3 | 7 | 36 |

Ex. = Example, CEx. = Comparative Example

It is seen from the results in Table 3 that Examples 1 to 3 are almost free of the leakage of water as compared with Comparative Examples 1 to 3.

TABLE 4

(Degradability evaluation results)

| Ex. and CEx. | Tensile strength after immersion for 4 weeks (MPa) | Tensile strength after immersion for 8 weeks (MPa) | Tensile strength after immersion for 12 weeks (MPa) |
| --- | --- | --- | --- |
| Ex. 1 | 3.5 | 2.0 | 1.5 |
| Ex. 2 | 4.5 | 3.3 | 0.9 |
| Ex. 3 | 19.8 | 8.6 | 4.5 |
| CEx. 1 | 4.0 | 1.3 | 0 |
| CEx. 2 | 7.7 | 6.6 | 6.7 |
| CEx. 3 | 3.3 | 2.0 | 1.0 |

Ex. = Example, CEx. = Comparative Example

It is seen from the results in Table 4 that Examples 1 to 3 are excellent over Comparative Examples 1 and 3 in the performance of maintaining strength. Further, Comparative Example 2 has almost no decrease in strength and it is expected that the artificial dura mater in Comparative Example 2 remains undesirably in an organ for a long period of time.

[Animal Test]

The artificial dura maters in Example 1 and Comparative Example 2 were used for a implantation test of in a rabbit cephalic part.

(Test Method)

Rectangular holes having a size of about 8 mm×14 mm each were bored in temporal regions on both sides of a rabbit cranial bone, and autodura maters having a size of 8 mm×10 m each were extracted. Then, the defect portions were covered with the artificial dura maters having a size of 9 mm×15 mm each. In this case, blood discharged was not removed so long as such was possible, and the artificial dura maters were placed directly on the brain surface. Three months after the implantation, the craniotomy was carried out again to see states of adhesion between each artificial dura mater and the brain surface. This test was carried out with regard to 20 cases, and the artificial dura mater of Example 1 and the artificial dura mater of Comparative Example 2 were compared as regards the adhesion occurrence ratio. Table 5 shows the results.

TABLE 5

(Animal test results)

|  | Artificial dura mater of Example 1 | Artificial dura mater of Comparative Example 2 |
| --- | --- | --- |
| Number of case of adhesion/ Number of cases tested | 1/20 | 8/20 |
| Rate of adhesion occurrence | 5% | 40% |

It is seen from the results of Table 5 that the artificial dura mater of Example 1 clearly has a smaller rate of adhesion occurrence than that of the artificial dura mater of Comparative Example 2.

INDUSTRIAL UTILITY

The artificial dura mater of this invention basically comprises a substrate layer and a stacked material layer and is free of liquid leakage since the bloating of suture holes is small even without further stacking such two layers having different functions (an elastic layer and a form-retaining layer) in addition to a leakage-preventing layer as those in the conventional artificial dura maters. Further, it is expected that even when produced by melt-molding, the artificial dura mater of this invention maintains its strength in an organ for approximately 3 months or more which is a little longer than a period required for the regeneration of an autodura mater. The industrial utility thereof is hence remarkably large.

The invention claimed is:

1. An artificial dura mater comprising a laminate of at least two layers of in vivo degradable polymers, at least one layer of them being a substrate layer, said substrate layer being formed of a lactic acid/glycolic acid/ε-caprolactone copolymer, said copolymer having a lactic acid/glycolic acid/ε-caprolactone component molar ratio of 60-85:3-15:10-30 mol % and the copolymer having an average chain length that satisfies the following expressions (1) to (3), $$2<L(LA)<[LA\%/(LA\%+GA\%+CL\%)]\times X\times 0.058 \quad (1)$$

$$1<L(GA)<[GA\%/(LA\%+GA\%+CL\%)]\times X\times 0.58 \quad (2)$$

$$1<L(CL)<[CL\%/(LA\%+GA\%+CL\%)]\times X\times 0.58 \quad (3)$$

wherein $L(LA)$ is an average chain length of lactic acid units, $L(GA)$ is an average chain length of glycolic acid units, $L(CL)$ is an average chain length of caprolactone units, $LA\%$ is a molar ratio of a lactic acid component in the copolymer, $GA\%$ is a molar ratio of a glycolic acid component in the copolymer, $CL\%$ is a molar ratio of a caprolactone component in the copolymer and $X$ is a polymerization degree of the copolymer, wherein said copolymer is obtained by a two-step polymerization process which comprises the steps of (1) carrying out polymerization to produce a lactic acid/glycolic acid/ε-caprolactone copolymer with a component molar ratio of 60-94:3-20:3-37 mol %, and (2) adding a monomer mixture for constituting a lactic acid/glycolic acid/ε-caprolactone copolymer to the copolymer in (1) to obtain a lactic acid/glycolic acid/ε-caprolactone copolymer having a lactic acid/glycolic acid/ε-caprolactone component molar ratio of 60-85:3-15:10-30 mol % as a final product.

2. The artificial dura mater of claim 1, wherein said copolymer has a metal content of 60 ppm or less.

3. The artificial dura mater of claim 1, wherein said copolymer has a monomer content, as a total content of lactic acid, glycolic acid and ε-caprolactone, of 40 ppm or less.

4. The artificial dura mater of claim 1, wherein a fluid leakage from a suture portion is 5 ml/minute or less at a brain pressure of 20 mmHg or less when the artificial dura mater is sutured to an organic brain dura material.

5. The artificial dura mater of claim 1, wherein a hydrophilic polymer layer is stacked on one surface or both surfaces of said substrate layer, the hydrophilic polymer layer being a stacked material layer that works to prevent adhesion thereof to a brain surface.

6. The artificial dura mater of claim 5, wherein the hydrophilic polymer constituting said stacked material layer is a water-swelling polymer.

7. An artificial dura mater of claim 1 formed by stacking two or more layers of in vivo degradable polymers by melt-molding, at least one layer of substrate layers being formed of a lactic acid/glycolic acid/ε-caprolactone copolymer, said copolymer having a lactic acid/glycolic aciciis-caprolactone component molar ratio of 60-85:3-15:10-30 mol %, the copolymer having a metal content of 60 ppm or less and having a monomer content, as a total content of lactic acid, glycolic acid and ε-caprolactone monomers, of 40 ppm or less.

8. A process for the production of a substrate layer for an artificial dura mater comprising a laminate of at least two layers of in vivo degradable polymers, at least one layer of them being the substrate layer, said substrate layer being formed of a lactic acid/glycolic acid/ε-caprolactone copolymer, said copolymer having a lactic acid/glycolic acid/ε-caprolactone component molar ratio of 60-85:3-15:10-30 mol % and the copolymer having an average chain length that satisfies the following expressions (1) to (3), $$2 < L(LA) < [LA\%/(LA\%+GA\%+CL\%)] \times X \times 0.058 \quad (1)$$

$$1 < L(GA) < [GA\%/(LA\%+GA\%+CL\%)] \times X \times 0.58 \quad (2)$$

$$1 < L(CL) < [CL\%/(LA\%+GA\%+CL\%)] \times X \times 0.58 \quad (3)$$

wherein $L(LA)$ is an average chain length of lactic acid units, $L(GA)$ is an average chain length of glycolic acid units, $L(CL)$ is an average chain length of caprolactone units, LA% is a molar ratio of a lactic acid component in the copolymer, GA% is a molar ratio of a glycolic acid component in the copolymer, CL% is a molar ratio of a caprolactone component in the copolymer and $X$ is a polymerization degree of the copolymer, wherein the process for producing said substrate layer comprises,
- (1) carrying out polymerization to produce a lactic acid/glycolic acid/ε-caprolactone copolymer with a component molar ratio of 60-94:3-20:3-37 mol %,
- (2) adding a monomer mixture for constituting a lactic acid/glycolic acid/ε-caprolactone copolymer to the copolymer in (1) to obtain a lactic acid/glycolic acid/ε-caprolactone copolymer having a lactic acid/glycolic acid/ε-caprolactone component molar ratio of 60-85:3-15:10-30 mol % as a final product, and
- (3) forming the above substrate layer from the copolymer obtained by the above steps (1) and (2).

9. A process for the production of the artificial dura mater, which comprises stacking hydrophilic polymer layer on one surface or both surfaces of the substrate layer produced in claim 8, the hydrophilic polymer layer being a stacked material layer that works to prevent adhesion thereof to a brain surface.

* * * * *